United States Patent
Parikh et al.

(10) Patent No.: US 12,156,930 B2
(45) Date of Patent: Dec. 3, 2024

(54) HAIR COSMETIC COMPOSITIONS CONTAINING SUGAR ALCOHOL, SACCHARIDE COMPOUND, AND PECTIN AND METHODS OF USE

(71) Applicant: L'OREAL, Paris (FR)

(72) Inventors: Dhara Parikh, New Brunswick, NJ (US); Vanessa Comeron-Decarlo, Roselle Park, NJ (US); Aziza Khader Suleiman, Paterson, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/805,032

(22) Filed: Feb. 28, 2020

(65) Prior Publication Data

US 2021/0267871 A1    Sep. 2, 2021

(51) Int. Cl.

| | |
|---|---|
| *A61K 8/60* | (2006.01) |
| *A61K 8/34* | (2006.01) |
| *A61K 8/73* | (2006.01) |
| *A61K 8/92* | (2006.01) |
| *A61K 8/9783* | (2017.01) |
| *A61Q 5/06* | (2006.01) |

(52) U.S. Cl.
CPC ............. *A61K 8/731* (2013.01); *A61K 8/34* (2013.01); *A61K 8/345* (2013.01); *A61K 8/60* (2013.01); *A61K 8/73* (2013.01); *A61K 8/732* (2013.01); *A61K 8/922* (2013.01); *A61K 8/9783* (2017.08); *A61Q 5/06* (2013.01); *A61K 2800/30* (2013.01); *A61K 2800/34* (2013.01); *A61K 2800/48* (2013.01); *A61K 2800/49* (2013.01); *A61K 2800/52* (2013.01)

(58) Field of Classification Search
None
See application file for complete search history.

(56) References Cited

U.S. PATENT DOCUMENTS

| | | | |
|---|---|---|---|
| 5,690,981 A * | 11/1997 | Watanabe | A23L 13/65 426/573 |
| 9,918,922 B1 | 3/2018 | Botto et al. | |
| 10,617,613 B2 | 4/2020 | Botto et al. | |
| 2012/0164092 A1 * | 6/2012 | Kurashima | A61K 8/86 424/70.11 |
| 2013/0287708 A1 * | 10/2013 | Silberstein | A61K 8/64 514/25 |

FOREIGN PATENT DOCUMENTS

| | | | | |
|---|---|---|---|---|
| CA | 2822227 A1 * | 6/2012 | ............ | A61K 8/042 |
| DE | 10361069 A1 * | 7/2005 | ......... | B05B 11/0043 |
| JP | 02145158 | * 6/1990 | | |
| JP | 2010189358 | * 9/2010 | ............ | A61K 8/365 |
| WO | 20190119080 | 6/2019 | | |

OTHER PUBLICATIONS

Signature Filling Company. http://signaturefillingcompany.com/benefits-bag-valve-aerosol-packaging/. Published: Jun. 15, 2018.*
JP02145158 Eng Tran. Published: Jun. 1990.*
Henry. https://jorganicsolutions.com/blogs/news/everything-you-need-to-know-about-humectants-for-your-natural-hair#comments. Published: Apr. 3, 2022.*
DE10361069 Eng Tran. Published: Jul. 21, 2005.*
Barbe. Oral Diseases. 2019;25:1519-1529. Published: Sep. 2019.*
JP2010189358 Eng Tran. Published: Sep. 2, 2010.*
International Search Report and Written Opinion issued on Jun. 4, 2021 for corresponding PCT Application No. PCT/US2021/018370.
Database GNPD; Mintel; "Shaping Jelly", 2019; XP055797447.
Database GNPD; Mintel; "Serum", 2019; XP055797450.

* cited by examiner

*Primary Examiner* — Nicole P Babson
*Assistant Examiner* — Lori K Mattison
(74) *Attorney, Agent, or Firm* — POLSINELLI PC

(57) ABSTRACT

The present disclosure relates to hair cosmetic compositions comprising: (a) at least one sugar alcohol: (b) at least one saccharide compound, and mixtures thereof; (c) pectin; (d) at least one water-soluble solvent; and (e) water. The hair cosmetic compositions provide excellent hair styling benefits without requiring synthetic film-forming polymers and/or silicones. In particular, the hair cosmetic compositions are useful for imparting to hair, durable styling or shaping benefits, curl definition, curl regularity, shape/styling control, shine, and frizz control.

25 Claims, No Drawings

HAIR COSMETIC COMPOSITIONS CONTAINING SUGAR ALCOHOL, SACCHARIDE COMPOUND, AND PECTIN AND METHODS OF USE

FIELD OF THE DISCLOSURE

The present disclosure relates to hair cosmetic compositions for treating and/or styling/shaping hair. The hair cosmetic compositions contain a combination of sugar alcohol(s), saccharide compounds, and pectin, and are useful in methods for imparting to hair, durable styling or shaping benefits, curl definition, curl regularity, shape/styling control, shine, and frizz control.

BACKGROUND

Consumers desire new multi-functional hair products that can impart good styling benefits to hair, are durable, and impart certain cosmetic characteristic to the hair. Such products should be pleasing to the senses, have innovative, interesting and/or pleasing textures, without loss in functional performance. Furthermore, many consumers prefer hair products that provide a light feel, are easy to apply, and add shine and luster to the hair.

Traditional hair products on the cosmetic market appear in various forms. They range anywhere from solutions, foams, gels, creams, waxes, mousses, sprays, serums, to aerosols and can impart a variety of levels of benefits to the hair depending on the state of the hair and the components of the product. Generally, products that are designed to impart styling or shaping benefits to hair are in the form of hair styling or hair care/hair treatment products. Some of these products are often sticky or tacky upon application and once dry, may become stiff and/or "crunchy" (i.e. the film is hard and brittle resulting in a crunching feel or sound when the hair is touched), which is undesirable for many consumers.

Current products for imparting styling or shaping benefits to hair often include water soluble film-forming polymers. Depending on the chemical make-up of these polymers, they may be either soluble in water, or they may be water insoluble polymers which are made water soluble via various chemical modifications, such as neutralization. Solutions comprising these polymers tend to be viscous, i.e. as the concentration of the polymer increases, its viscosity builds up rapidly. Translated to styling applications, as the solvent evaporates, the polymer solution becomes thicker on the hair surface, resulting in a sticky or tacky film.

SUMMARY OF THE DISCLOSURE

The instant disclosure relates to hair cosmetic compositions, in particular, hair styling compositions that are unique in their ability to impart a variety of desirable properties to hair. For example, the compositions maintain the shape of hair, achieve long-lasting frizz control, provide strong styling hold, and impart a pleasant texture and body to the hair. Furthermore, upon application to the hair, the compositions have a clean, natural, and light-weight feel.

The hair cosmetic compositions include: (a) at least one sugar alcohol; (b) at least one saccharide compound; (c) pectin; (d) at least one water-soluble solvent; and (e) water. Typically, the total amount of sugar alcohol(s) is equal to or less than the total amount of saccharide compound (b); the total amount of saccharide compound (b) is greater than the total amount of pectin; and the total amount of sugar alcohol(s), saccharide compound (b), and pectin is at least 2 wt. %, based on the total weight of the composition. Also, the hair cosmetic compositions usually include a high amount of water, for example, at least 70 wt. % of water, based on the total weight of the composition.

Non-limiting examples of sugar alcohols include isomalt, mannitol, sorbitol, xylitol, lactitol, maltitol, inositol, erythritol, hydrogenated starch hydrolysates, and mixtures thereof. In some cases, the hair cosmetic composition includes at least sorbitol.

Non-limiting example of useful water-soluble solvents include organic solvent, monomeric polyols, a glycol, glycerin, a polyhydric alcohol, C1 to C8 monoalcohols, and a mixture thereof. Exemplary monomeric polyols that may be included in the hair styling compositions include, but are not limited to, glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol. Additional non-limiting examples of polyols that have one or more aliphatic diols include 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and mixtures thereof.

Additional components may also optionally be included in the hair cosmetic compositions, as set forth throughout the instant disclosure. Likewise, components may be excluded from the hair cosmetic compositions. For instance, in some cases, the hair cosmetic compositions are essentially free of synthetic film-forming polymers. In some cases, the hair cosmetic compositions are essentially free of silicones.

Finally, hair cosmetic compositions may be used in various methods for treating hair, for example, human hair, including human hair of an individual's head. For example, the compositions are useful for: (i) improving or retaining curl definition of hair; (ii) imparting humidity resistance to hair; (iii) reducing hair frizz; (iv) controlling hair volume; (v) styling or shaping hair; (vi) straightening hair; and (vi) improving the appearance of hair.

DETAILED DESCRIPTION OF THE DISCLOSURE

The hair cosmetic composition of the instant disclosure includes a unique combination of sugar alcohol(s), saccharide compound, and pectin. The synergy amongst these components results in compositions that provide desirable softening attributes, holding ability, and styling properties to hair. More specifically, the hair cosmetic compositions contain:

(a) at least one sugar alcohol;
(b) at least one saccharide compound;
(c) pectin;
  wherein
    the total amount of sugar alcohol(s) is equal to or less than the total amount of saccharide compound (b),
    the total amount of saccharide compound (b) is greater than the total amount of pectin, and
    the total amount of sugar alcohol(s), saccharide compound (b), and pectin is at least 0.5 wt. %, based on the total weight of the hair cosmetic composition;
(d) at least one water-soluble solvent; and
(e) water.

For example, the total amount of the combination of sugar alcohol(s), saccharide compound (b) and pectin may be from at least 0.5 wt. % to about 10 wt. %, based on the total weight of the composition. In some instances, the total amount of the combination of sugar alcohol(s), saccharide compound (b) and pectin may be from at least 0.75 wt. % or at least 1 wt. % or at least 1.5 wt. % or at least 2 wt. % or at least 2.5 wt. % or at least 3 wt. %, or at least 3.5 wt. % or for example, from at least 1 wt. % to about 10 wt. %, from at least 1.5 wt. % to about 10 wt. %, from at least 2 wt. % to about 10 wt. %, from at least 2.5 wt. % to about 10 wt. %, from at least 3 wt. % to about 10 wt. %, from at least 3.5 wt. % to about 10 wt. %, from at 3.8 wt. % to about 10 wt. %, from at least 1 wt. % to about 8 wt. %, from at least 2 wt. % to about 8 wt. %, from at least 2.5 wt. % to about 8 wt. %, from at least 2.5 wt. % to about 6 wt. %, from at least 3 wt. % to about 8 wt. %, from at least 3 wt. % to about 6 wt. %, or from at least 3 wt. % to about 5 wt. %, including all ranges and sub-ranges there between, based on the total weight of the hair cosmetic composition.

The total individual amount of sugar alcohol(s), saccharide compound (b) and pectin can vary with respect to each other, but in some instances, the total amount of sugar alcohol(s) is equal to or less than the total amount of saccharide compound (b) in the hair cosmetic compositions. Additionally, (or alternatively), in some instances, the total amount of saccharide compound (b) is greater than the total amount of pectin in the hair cosmetic compositions.

If the total amount of sugar alcohol(s) is equal to or less than the total amount of saccharide compound (b) in the hair cosmetic compositions, the weight ratio of sugar alcohol(s) (a) to saccharide compound (b) may be 1 or less, such as from about 0.1 to about 1, or from about 0.2 to about 1 or from about 0.3 to about 1, or from about 0.4 to about 1, or from about 0.5 to about 1 or from about 0.6 to about 1, or from about 0.7 to about 1, or from about 0.75 to about 1, or from about 0.8 to about 1, or from about 0.9 to about 1, including all ranges and sub-ranges there between.

In some cases, the ratio of sugar alcohol(s) to pectin may be from about 2 to about 10, or from about 2 to about 8, or from about 2.5 to about 7.5, or from about 3 to about 7 or from about 3.5 to about 6.5, or from about 4 to about 6 or from about 4.5 to about 5.5, including all ranges and sub-ranges there between.

If the total amount of saccharide compound (b) is greater than the total amount of pectin in the hair cosmetic compositions, the ratio of saccharide compound (b) to pectin may be from about 1.2 to about 10, or from about 1.5 to about 10, or from about 2 to about 10, or from about 2.5 to about 10, or from about 3 to about 10, or from about 3.5 to about 10, or from about 4 to about 10, or from about 4.5 to about 9, or from about 4.5 to about 8, or from about 5 to about 7.5, or from about 5.5 to about 7, or from about 6 to about 7, including all ranges and sub-ranges there between.

Sugar Alcohols

A sugar alcohol is a polyalcohol resulting from the reduction of the carbonyl group in a monosaccharide to a hydroxyl group. Non-limiting examples of sugar alcohols include isomalt, mannitol, sorbitol, xylitol, lactitol, maltitol, inositol, erythritol, hydrogenated starch hydrolysates, and mixtures thereof. In some cases, the hair cosmetic compositions include at least sorbitol.

The total amount of the one or more sugar alcohols can vary but is typically about 0.1 to about 10 wt. %, based on the total weight of the hair cosmetic composition. In some cases, the total amount of the one or more sugar alcohols may be from about 0.2 to about 8 wt. %, or from about 0.3 to about 7.5 wt. %, or from about 0.4 to about 7 wt. %, or from about 0.5 to about 6 wt. %, or from about 1 to about 5 wt. %, or from about 1.2 to about 4 wt. %, or from about 1.5 to about 3 wt. %, including all ranges and sub-ranges there between, based on the total weight of the hair cosmetic composition.

Saccharide Compounds

Suitable saccharide compounds of the present disclosure may be selected from monosaccharides, disaccharides, polysaccharides, and mixtures thereof.

Suitable examples of saccharide compounds are glucose, sucrose, maltodextrin, cellulose, and a mixture thereof.

In one embodiment, the saccharide compounds of the present disclosure are selected from monosaccharides, disaccharides, and mixtures thereof.

In one embodiment, the saccharide compounds of the present disclosure include at least one monosaccharide.

In one embodiment, the saccharide compounds of the present disclosure includes at least one disaccharide.

In one embodiment, the saccharide compounds of the present disclosure are selected from glucose, sucrose, and a mixture thereof.

In one embodiment, the saccharide compounds of the present disclosure include polysaccharides selected from maltodextrin, cellulose, or a mixture thereof.

The total amount of saccharide compound (b) in the hair cosmetic composition can vary and is non-limited. Nonetheless, in some instances, the total amount of saccharide compound (b) may be about 0.1 to about 6 wt. %, based on the total weight of the hair cosmetic composition. In some cases, the total amount of saccharide compound (b) may be from about 0.1 to about 6 wt. %, or from about 0.2 to about 5.5 wt. %, or from about 0.5 to about 5 wt. %, or from about 0.75 to about 5 wt. %, or from about 1 to about 5 wt. %, or from about 1.2 to about 4 wt. %, or from about 1.5 to about 3 wt. %, including all ranges and sub-ranges there between, based on the total weight of the hair cosmetic composition.

Pectin

The total amount of pectin in the hair cosmetic composition can also vary and is non-limited. Nonetheless, in some instances, the total amount of pectin in the hair cosmetic compositions is about 0.05 to about 5 wt. %, based on the total weight of the hair cosmetic composition. In some cases, the total amount of pectin is from about 0.05 to about 4 wt. %, or from about 0.1 to about 3.5 wt. %, or from about 0.1 to about 3 wt. %, or from about 0.1 to about 2.5 wt. %, or from 0.1 to about 2 wt. %, or from about 0.1 to about 1.8 wt. %, or from about 0.2 to about 1.5 wt. %, or from about 0.3 to about 1 wt. %, including all ranges and sub-ranges there between, based on the total weight of the hair cosmetic composition.

Water-Soluble Solvents and Water

The hair cosmetic compositions include at least one water-soluble solvent, such as, for example, an organic solvent. The term "water-soluble solvent" denotes a compound that is liquid at room temperature and water-miscible (miscibility in water of greater than 50% by weight at 25° C. and atmospheric pressure).

Non-limiting examples of water-soluble solvents include lower monoalcohols and monomeric polyols. Non-limiting examples of lower monoalcohols are those containing from 1 to 8 carbon atoms, such as ethanol and isopropanol, glycols containing from 2 to 8 carbon atoms, such as ethylene glycol, propylene glycol, 1,3-butylene glycol and dipropylene glycol, caprylyl glycol, $C_3$ and $C_4$ ketones and $C_2$-$C_4$ aldehydes.

Non-limiting examples of water-soluble organic solvents that may be mentioned include linear or branched $C_2$-$C_4$ alkanols, such as ethanol and isopropanol; polyols and polyol ethers, for instance 2-butoxyethanol, glycerol, propylene glycol, dipropylene glycol, polyethylene glycols, propylene glycol monomethyl ether, diethylene glycol monomethyl ether and monoethyl ether, and also aromatic alcohols, for instance benzyl alcohol or phenoxyethanol, and mixtures thereof. In some cases, glycerol (also known as glycerin) is particularly useful.

In some cases, the one or more water-soluble solvents include one or more monomeric polyols. Non-limiting examples of monomeric polyols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol. Non-limiting examples of monomeric polyols having one or more aliphatic diols include 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and mixtures thereof.

The total amount of the one or more water-soluble solvents can vary but is typically about 0.5 to about 25 wt. %, based on the total weight of the hair cosmetic composition. In some cases, the total amount of the water-soluble solvent(s) is about 1 to about 20 wt. %, about 1 to about 15 wt. %, about 1 to about 10 wt. %, about 2 to about 25 wt. %, about 2 to about 20 wt. %, about 2 to about 15 wt. %, about 2 to about 10 wt. %, about 3 to about 25 wt. %, about 3 to about 20 wt. %, about 3 to about 15 wt. %, or about 3 to about 10 wt. %, including all ranges and sub-ranges there between, based on the total weight of the hair cosmetic composition.

The hair cosmetic compositions include water, which is often the predominant ingredient in the hair cosmetic compositions, such as hair styling. Therefore, the hair cosmetic compositions may be referred to as "aqueous hair cosmetic compositions". In some embodiments, when the hair cosmetic compositions of the present disclosure are employed as hair styling compositions, the hair cosmetic compositions may also be referred to as "aqueous hair styling compositions" such as "aqueous leave-on hair styling compositions." The total amount of water can vary, but typically the total amount of water in the hair cosmetic compositions is at least 70 wt. %, based on the total weight of the composition. For example, the total amount of water may be at least 70 wt % to about 95 wt %, at least 70 wt. % to about 92 wt. %, at least 75 wt. % to about 95 wt. %, at least 75 wt. % to about 92 wt. %, at least 80 wt. % to about 95 wt. %, at least 80 wt. % to about 92 wt. %, at least 85 wt. % to about 95 wt. %, at least 85 wt. % to about 92 wt. %, including all ranges and sub-ranges there between, based on the total weight of the hair cosmetic composition.

In some instances, the hair cosmetic compositions of the present disclosure include at least one stabilizer and/or thickening agent The stabilizer and/or thickening agent(s) may be thickening polymers. Non-limiting examples include acacia, agar, algin, alginic acid, ammonium alginate, amylopectin, calcium alginate, sodium alginate, calcium carrageenan, carnitine, carrageenan, dextrin, gelatin, gellan gum, guar gum, tragacanth gum, acacia gum, Arabic gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sodium carboxymethyl dextran, sodium carrageenan, tragacanth gum, xanthan gum, modified xanthan gum, biosacharide gum, chitin, levan, elsinan, collagen, gelatin, zein, gluten, soy protein, casein, and mixtures thereof. In some cases, carrageenan is a particularly preferred stabilizer/thickening agent.

Other non-limiting examples of thickening polymers include pullulan, hydroxypropylmethyl cellulose, hydroxyethyl cellulose, hydroxypropyl cellulose, polyvinyl pyrrolidone, carboxymethyl cellulose, polyacrylic acid, methylmethacrylate copolymer, carboxyvinyl polymer, dextrin, polyvinyl alcohol, carboxylated polyvinylalcohol, sulfonated polyvinyl alcohol, starch, starch derivatives, hemicellulose, hemicellulose derivatives, proteins, chitosan, chitosan derivatives, polyethylene glycol, tetramethylene ether glycol, hydroxymethyl cellulose, and mixtures thereof. In some cases, the one or more thickening polymers may be sodium alginate, xanthan gum, modified xanthan gum, tragacanth gum, guar gum, acacia gum, Arabic gum, and mixtures thereof. In some cases, carrageenan is particularly useful.

In some instances, the stabilizer and/or thickening agent(s) is other than the saccharide compounds of the present disclosure.

In some instances, the saccharide compounds of the present disclosure may function as a stabilizer and/or thickening agent(s) in the compositions of the present disclosure.

The total amount of the stabilizer and/or thickening agent(s) may vary, but is typically about 0.01 to about 10 wt. %, based on the total weight of the hair cosmetic composition. In some cases, the total amount of stabilizer and/or thickening agent(s) is about 0.01 to about 8 wt. %, about 0.01 to about 6 wt. %, about 0.01 to about 5 wt. %, about 0.05 to about 10 wt. %, about 0.05 to about 8 wt. %, about 0.05 to about 6 wt. %, about 0.05 to about 5 wt. %, or about 0.1 to about 10 wt. %, about 0.1 to about 8 wt. %, about 0.1 to about 6 wt. %, or about 0.1 to about 5 wt. %, including all ranges and sub-ranges therebetween, based on the total weight of the hair cosmetic composition.

In some instances, the hair cosmetic compositions of the present disclosure may include at least one surfactant, such as one or more nonionic surfactant, anionic surfactant, cationic surfactant, amphoteric/zwitterionic surfactant. Nonionic surfactants can be particularly useful in some cases. Non-limiting examples of useful nonionic surfactants include glyceryl esters, ethylene glycol esters, propylene glycol esters and sucrose esters of fatty acids. More specifically, in some cases, the hair styling compositions may optionally include one or more polyglycrol esters. A more exhaustive but non-limiting listing of useful surfactants that may optionally be included (or excluded) from the hair cosmetic composition is provided later, under the heading "Surfactants."

The total amount of the surfactant(s) in the hair cosmetic composition, if present, may vary but may be about 0.01 to about 10 wt. %, based on the total weight of the hair cosmetic composition. In some cases, the total amount of surfactant(s) in the hair cosmetic composition, if present, is about 0.01 to about 8 wt. %, about 0.01 to about 6 wt. %, about 0.01 to about 5 wt. %, about 0.05 to about 10 wt. %, about 0.05 to about 8 wt. %, about 0.05 to about 6 wt. %, about 0.05 to about 5 wt. %, about 1 to about 10 wt. %, about 1 to about 8 wt. %, about 1 to about 6 wt. %, or about 1 to about 5 wt. %, including all ranges and sub-ranges there between, based on the total weight of the hair cosmetic composition.

The hair cosmetic compositions of the instant disclosure are unique in that they do not require synthetic polymers such as synthetic film-forming polymers. In fact, the hair cosmetic compositions do not necessarily require any synthetic ingredients. In some cases, synthetic film-forming polymer or synthetic polymer may be included but in other cases, they may be excluded. The term "synthetic polymer" (or "synthetic film-forming polymer") means a polymer, which is purely synthetic, or not of natural origin, especially those polymers, which are made by radical polymerization of ethylenically unsaturated monomers or by polycondensation. The term "natural polymer" means a polymer of natural origin, which includes those that have been subsequently chemically or physically modified (but retains at least 50% of its molecular structure from the original natural source). In particular, the term "natural original ingredient" refers to one of the following:

1. An ingredient which remains unchanged from its natural state; or
2. An ingredient which has undergone chemical or other processing which modifies it from its natural state but which retains at least 50% of its molecular structure from the original natural source.

In general, a naturally derived ingredient is processed to improve its stability, efficacy and/or safety for use in hair cosmetic products. The degree of processing varies for each ingredient, but at the end only an ingredient that retains at least 50% of its molecular structure from the original natural source is considered natural origin. In some cases, the hair cosmetic compositions of the instant disclosure are "natural hair cosmetic compositions." A "natural hair cosmetic composition" may include a leave-on hair styling composition comprising only "natural original ingredients," as defined above.

Non-limiting examples of synthetic film-forming polymers (which in some cases may be excluded from the instant hair cosmetic compositions) include non-ionic hair-fixing polymers (e.g., copolymerizates of vinyl pyrrolidone and vinyl acetate, terpolymers of vinyl pyrrolidone, vinyl acetate and vinyl propionate, polyacrylamides, polyvinyl alcohols and polyethylene glycol/polypropylene glycol copolymers. Polyvinyl pyrrolidone, polyvinyl caprolactam and their copolymers with at least one further nonionic monomer, for example, polyvinylpyrrolidone/vinyl acetate copolymers) and anionic hair-fixing polymers such as synthetic homo- or copolymers with neutralizable monomer units containing acid groups, which are copolymerizable with comonomers, if necessary, which contain no acid groups. The acid groups may include —COOH, —SO$_3$H, —OSO$_3$H, —OPO$_2$H, —PO$_3$H$_2$. The acid groups can be unneutralized, or partially or completely neutralized.

Furthermore, the leave-in hair styling compositions do not require silicones (silicone and silicone containing materials). Non-limiting examples of silicones (which may optionally excluded from the instant hair cosmetic compositions) include dimethicone, dimethiconol, amodimethicone, cyclomethicones, amino-modified silicones, and polyether-modified silicones.

In some instances, the leave-in hair styling composition do not require alcohols, in particular, monohydric alcohols (monoalcohols). Non-limiting examples of monohydric alcohols include lower monohydric alcohols having 8 carbons or less, having 6 carbons or less, or having 4 carbons or less.

All of the hair cosmetic compositions described throughout the disclosure may optionally be free or essentially free of synthetic ingredients, for example, synthetic film-forming polymers. Similarly, all of the hair cosmetic compositions described throughout the disclosure may be free or essentially free of silicones. Additionally, all of the hair cosmetic compositions described throughout the disclosure may be free or essentially free of lower monohydric alcohols having 8 carbons or less.

The hair cosmetic compositions described herein may be in any suitable physical form. Suitable forms include, but are not limited to low to moderate viscosity liquids, lotions, milks, mousses, sprays, gels, creams, pastes, clays, bars, conditioners, and the like. In some cases, the hair cosmetic composition is in the form of a spray formulation. Spray formulations may be dispensed from containers that include aerosol dispensers or pump spray dispensers. Such dispensers are known in the art and are commercially available from a variety of manufacturers. When the spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed. In some cases, the hair cosmetic compositions are in the form of a spray.

Regardless of the form of the hair cosmetic composition, in this case, the hair cosmetic compositions are typically not emulsions, i.e., the hair cosmetic compositions are not an oil-in-water emulsions, water-in-oil emulsions, silicone-in-water emulsions, or water-in-silicone emulsions. Accordingly, the hair cosmetic compositions do not require emulsifiers and therefore may be free or essentially free of emulsifiers.

When the hair cosmetic compositions of the instant disclosure are employed as leave-on hair styling compositions, as suggested by the term "leave-on hair styling compositions," these compositions are formulated so that they can remain on the hair for extended periods of time, i.e., the compositions are applied to the hair, for example, during styling of the hair and allowed to remain for one or more hours, or one or more days before being removed, for example, by washing. In other words, the leave-on hair styling compositions are applied to the hair and allowed to remain on the hair without immediate rinsing or removal. The leave-on hair styling compositions may be applied to the hair, for example, after shampooing, before or during the styling process. The hair may be wet, damp, or already dry when the hair styling composition is applied to the hair. In some cases, the leave-on hair styling composition may be applied to wet or damp hair after which the hair is blow dried and styled. In other cases, the hair may be previously dried and the leave-on hair styling composition is applied to dry hair, in order to treat, shape, or style the hair.

The hair cosmetic compositions may be packaged in a variety of different containers, such as, for example, a ready-to-use container. Non-limiting examples of useful packaging include tubes, jars, caps, unit dose packages, and bottles, including squeezable tubes and bottles, and canisters.

The hair cosmetic compositions may be used in various methods for treating hair, for example, human hair, including human hair one an individual's head. For example, the compositions are useful for: (i) improving or retaining curl definition of hair; (ii) imparting humidity resistance to hair; (iii) reducing hair frizz; (iv) controlling hair volume; (v) styling or shaping hair; (vi) straightening hair; and (vi) improving the appearance of hair; wherein the methods typically comprise applying a hair styling composition disclosed herein to the hair. These methods are particularly useful for average to fine hair. The hair styling compositions are useful in methods for imparting durable styling or shaping properties and/or frizz control to hair. The methods may include applying the hair cosmetic composition to the hair, subsequently styling the hair while allowing the hair cosmetic composition to remain on the hair, for example, for one or more hours, or one or more days before being removed by a subsequent washing. The hair cosmetic composition may be applied to wet, damp, or already dry hair and can be air dried or blow dried.

More exhaustive but non-limiting lists of components useful in the hair styling compositions disclosed herein are presented below.

Surfactants

Cationic Surfactants

The term "cationic surfactant" means a surfactant that is positively charged when it is contained in the composition according to the disclosure. This surfactant may bear one or more positive permanent charges or may contain one or more functions that are cationizable in the composition according to the disclosure.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Anionic Surfactants

The term "anionic surfactant" means a surfactant comprising, as ionic or ionizable groups, only anionic groups. These anionic groups are chosen preferably from the groups $CO_2H$, $CO_2^-$, $SO_3H$, $SO_3^-$, $OSO_3H$, $OSO_3^-$ $O_2PO_2H$, $O_2PO_2H$ and $O_2PO_2^{2-}$.

The anionic surfactant(s) that may be used may be alkyl sulfates, alkyl ether sulfates, alkylamido ether sulfates, alkylaryl polyether sulfates, monoglyceride sulfates, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used.

Mention is also made of $(C_6$-$C_{24})$alkyl sulfates, $(C_6$-$C_{24})$ alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts. In some cases, the anionic surfactant(s) are chosen from $(C_{10}$-$C_{20})$alkyl ether sulfates, and in particular sodium lauryl ether sulfate containing 2.2 mol of ethylene oxide.

Amphoteric Surfactants

Amphoteric surfactants useful in the cosmetic compositions disclosed herein may be chosen from betaines, sultaines, amphoacetates, amphoproprionates, and mixtures thereof. More typically, betaines and amphoproprionates are used, and most typically betaines. Betaines which can be used in the current compositions include those having the formulas below:

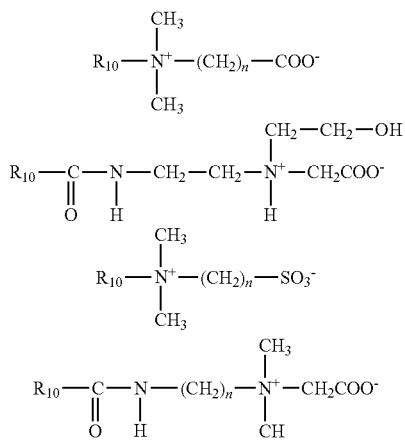

wherein $R^{10}$ is an alkyl group having 8-18 carbon atoms; and n is an integer from 1 to 3.

Particularly useful betaines include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocoamidopropyl betaine, behenyl betaine, capryl/capramidopropyl betaine, lauryl betaine, and mixtures thereof, and more typically coco betaine.

Hydroxyl sultaines useful in the compositions of the invention include the following

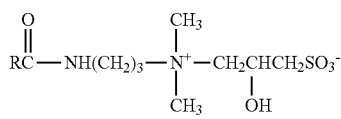

wherein
R is an alkyl group having 8-18 carbon atoms.
Useful alkylamphoacetates include those having the formula

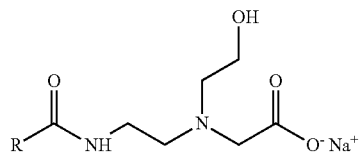

wherein
R is an alkyl group having 8-18 carbon atoms.
useful alkyl amphodiacetates include those having the formula

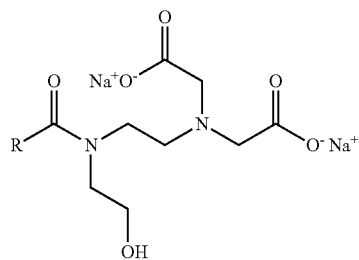

wherein
R is an alkyl group having 8-18 carbon atoms.

The amphoteric surfactants of the present disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Non-Ionic Surfactants

Nonionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

The nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1 N by Goldschmidt (CTFA name: glyceryl stearate SE), can also be used.

Cationic Conditioning Agents

The cationic conditioning agents that may be employed in the compositions of the present disclosure can be a monoalkyl quaternary amine, such as stearyltrimonium chloride, soyatrimonium chloride or coco-ethyldimonium ethosulfate. Other suitable cationic conditioning agents include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic conditioning agents may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic conditioning agents are cationic polymers. The term "cationic polymer" means any polymer comprising at least one cationic group and/or at least one group that may be ionized into a cationic group.

Particularly useful cationic polymers in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Particularly preferred cationic polymers of the present invention include POLYMER JR-125, POLYMER JR-400, Polymer JR-30M hydroxyethyl cellulosic polymers (polyquaternium 10) available from AMERCHOL; JAGUAR C® 13-S, guar hydroxypropyltrimonium chloride, available from Rhodia; and MERQUAT® 100 and 280, a dimethyl dialkyl ammonium chloride (polyquaternium 6) available from Nalco.

The cationic polymer is generally present in an amount of from greater than 0% to about 15%, preferably from about 0.5% to about 10% by weight, and more preferably from about 1% to about 5% by weight, based on the total weight of the composition.

Cationic polymers useful herein include polyquaternium 4, polyquaternium 6, polyquaternium 7, polyquaternium 10, polyquaternium 11, polyquaternium 16, polyquaternium 22, and polyquaternium 32. Cationic polymers useful in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, and guar hydroxypropyltrimonium chloride. Preferred cationic polymers include POLYMER JR-125, POLYMER JR-400, Polymer JR-30M hydroxyethyl cellulosic polymers (polyquaternium 10) available from AMERCHOL; JAGUAR C13-S, guar hydroxypropyltrimonium chloride, available from Rhodia; and MERQUAT 100 and 280, a dimethyl dialkyl ammonium chloride (polyquaternium 6) available from Nalco.

Oils

The hair styling composition may include one or more oils, for example, silicone oils, fluoro oils, hydrocarbon-based oils, etc. The term "oil" means any fatty substance which is in liquid form at room temperature (20-25° C.) and at atmospheric pressure (760 mmHg). Often, at least one of the oils in the cosmetic composition is part of an oily phase. An "oily phase" is a phase comprising at least one oil that may include additional liposoluble and lipophilic ingredients and the fatty substances. The oily phase can be combined with an aqueous phase in an emulsion. Oil that is suitable for use herein may be volatile or non-volatile. The term "volatile oil" relates to oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa ($10^{-3}$ to 300 mmHg). The term "non-volatile oil" relates to oil which remains on the skin or the keratin fiber, at room temperature and atmospheric pressure, for at least several hours and which in particular has a vapor pressure of less than $10^{-3}$ mmHg (0.13 Pa).

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. Further, suitable oil may be a mineral hydrocarbon-based oil, a plant hydrocarbon-based oil, or a synthetic hydrocarbon-based oil.

Silicone Oils

The cosmetic compositions described herein may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl) trimethylsiloxysilicates.

Other examples of silicone oils that may be mentioned include volatile linear or cyclic silicone oils, especially those with a viscosity 8 centistokes ($8 \times 10^6$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Fluoro Oils

The cosmetic compositions described herein may comprise one or more fluoro oils. For example, the one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The cosmetic compositions described herein may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the compositions include a synthetic oil selected from the group consisting of hydrogenated polyisobutene and hydrogenated polydecene.

The hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ≥10, for instance Purcellin oil (cetearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CCO by Cognis;

(viii) fatty amides, such as isopropyl N-lauroyl sarcosinate, such as the product sold under the trade name Eldew SL 205® from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

In certain instances, the non-volatile hydrocarbon-based oils are glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, such as octyldodecanol.

As volatile hydrocarbon-based oils, mention is made of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4, 6-pentamethylheptane), isodecane or isohexadecane, the oils sold under the Isopar or Permethyl trade names, branched C $C_8$-$C_{16}$ esters, and isohexyl neopentanoate.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldehyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The total amount of the one or more preservatives, when present, may vary. In some cases, the total amount of the one or more preservatives is about 0.01 to about 5 wt. %, about 0.01 to about 4 wt. %, about 0.15 to about 1 wt. %, or about 1 to about 3 wt. %, based on the total weight of the composition.

Suitable components, such as those listed in the instant disclosure (including those listed above), may be included or excluded from the hair styling compositions depending on the specific combination of other components, the form of the compositions, and/or the use of the formulation (e.g., hair spray, cream, paste, conditioner, etc.).

Water

The amount of water in the hair cosmetic compositions may be at least 50 wt. %, or from about 60 to about 95 wt. %, about 70 to about 95 wt. %, about 80 to about 95 wt. %, about 85 to about 95 wt. %, including all ranges and subranges there between, based on the weight of the composition.

Organic Solvents

The hair cosmetic compositions may optionally include at least one organic solvent (non-silicone solvents) other than the polyols of the present disclosure.

Non-limiting examples of organic solvents include, for example, alcohols (for example, C1-15, C1-10, or C1-6 alcohols, glycol ethers, or mixtures thereof.

Non-limiting examples of organic solvents include monoalcohols such as ethyl alcohol, isopropyl alcohol, propyl alcohol, benzyl alcohol, and phenylethyl alcohol, and glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

The total amount organic solvent(s) in the hair cosmetic composition, if present, can vary but is typically about 0.1 to about 10 wt. %, based on the total weight of the hair cosmetic composition. In some cases, the total amount of water-soluble solvent(s) is about 0.1 to about 8 wt. %, about 0.1 to about 6 wt. %, about 0.1 to about 0.5 to about 10 wt. %, about 0.5 to about 8 wt. %, about 0.5 to about 6 wt. %, about 0.5 to about 5 wt. %, about 1 wt. %, about 2 wt. %, about 3 wt. %, or about 4 wt. %, including all ranges and subranges there between, based on the weight of the composition.

Other Components

In one or more embodiments, the hair cosmetic compositions described herein may contain one or more additional ingredients. Examples include, but are not limited to surfactants, emulsifiers, thickeners (gums, polysaccharides other than pectin, polymers other than gums and polysaccharides), silicones, oils (natural or plant-based or synthetic), fillers, plant extracts, vitamins, fragrance, pH adjusters, chelants, and propellants. Additional details regarding such additional ingredients follows below.

Suitable examples of propellants are butane, isobutane, propane, hydrofluorocarbons, compressed air or nitrogen (aerosol type format).

In some instances, the hair cosmetic compositions of the instant disclosure include:
(a) from 0.1 to about 10 wt. %, or from about 0.2 to about 8 wt. %, or from about 0.3 to about 7.5 wt. %, or from about 0.4 to about 7 wt. %, or preferably, from about 0.5 to about 6 wt. %, or preferably, from about 1 to about 5 wt. %, or more preferably, from about 1.2 to about 4 wt. %, or even more preferably, from about 1.5 to about 3 wt. % of at least one sugar alcohol, preferably sorbitiol;
(b) from about 0.1 to about 6 wt. %, or from about 0.2 to about 5.5 wt. %, or from about 0.5 to about 5 wt. %, or from about 0.75 to about 5 wt. %, or preferably from about 1 to about 5 wt. %, or more preferably, from about 1.2 to about 4 wt. %, or even more preferably from about 1.5 to about 3 wt. %, of at least one saccharide compound selected from monosaccharides, disaccharides, and a mixture thereof, preferably glucose and/or sucrose;
(c) from about 0.05 to about 4 wt. %, or from about 0.1 to about 3.5 wt. %, or from about 0.1 to about 3 wt. %, or from about 0.1 to about 2.5 wt. %, or from about 0.1 to about 2 wt. %, or preferably from about 0.1 to about 1.8 wt. %, or more preferably, from about 0.2 to about 1.5 wt. %, or even more preferably, from about 0.3 to about 1 wt. %, of pectin;
wherein
the total amount of sugar alcohol(s) is equal to or less than the total amount of saccharide compound (b),
the total amount of saccharide compound (b) is greater than the total amount of pectin, and
the total amount of sugar alcohol(s), inulin, and sclerotium gum is at least 1 wt. %;
(d) at least one water-soluble solvent; and
(e) at least 70 wt. % of water;
all weights being based on the total weight of the hair cosmetic composition.

The one or more water-soluble solvents may include one or more monomeric polyols, for examples, those selected from the group consisting of glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol, and mixtures thereof.

In an embodiment, the one or more water-soluble solvents is glycerin.

In an embodiment, the one or more water-soluble solvents is propylene glycol.

In an embodiment, the one or more water-soluble solvents is caprylyl glycol.

In an embodiment, the one or more water-soluble solvents is butylene glycol.

In some instances, the hair cosmetic compositions of the instant disclosure include:
(a) from about 1 to about 5 wt. %, or from about 1.2 to about 4 wt. %, or from about 1.5 to about 3 wt. %, of at least one sugar alcohol, preferably sorbitiol;

(b) from about 1 to about 5 wt. %, or from about 1.2 to about 4 wt. %, or from about 1.5 to about 3 wt. %, of at least one saccharide compound selected from monosaccharides, disaccharides, and a mixture thereof, preferably glucose and/or sucrose;

(c) from about 0.1 to about 1.8 wt. %, or from about 0.2 to about 1.5 wt. %, or from about 0.3 to about 1 wt. %, of pectin;

wherein
the total amount of sugar alcohol(s) is equal to or less than the total amount of saccharide compound (b),
the total amount of saccharide compound (b) is greater than the total amount of pectin, and
the total amount of sugar alcohol(s), inulin, and sclerotium gum is from at least 1 wt. % to about 8 wt. %, or from at least 2 wt. % to about 8 wt. %, or from at least 2.5 wt. % to about 8 wt. %, or from at least 2.5 wt. % to about 6 wt. %;

(d) at least one water-soluble solvent selected from glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol, and mixtures thereof;

(e) at least 75 wt. % of water; and (f) from about 0.01 to about 10 wt. %, about 0.01 to about 8 wt. %, or about 0.05 to about 6 wt. % of at least one stabilizer and/or thickening agent, of example, a stabilizer and/or thickening agent selected from acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sodium carboxymethyl dextran, sodium carrageenan, tragacanth gum, xanthan gum, biosaccharide gum, and mixtures thereof; preferably, carrageenan;

all weights being based on the total weight of the hair cosmetic composition.

In some instances, the hair cosmetic compositions of the instant disclosure include:

(a) from about 0.5 to about 6 wt. %, or from about 1 to about 5 wt. %, or from about 1.2 to about 4 wt. %, or from about 1.5 to about 3 wt. %, of at least one sugar alcohol, including sorbitiol;

(b) from about 1 to about 5 wt. %, or from about 1.2 to about 4 wt. %, or from about 1.5 to about 3 wt. %, of at least one saccharide compound selected from monosaccharides, disaccharides, and a mixture thereof, preferably glucose and/or sucrose;

(c) from about 0.1 to about 1.8 wt. %, or from about 0.2 to about 1.5 wt. %, or from about 0.3 to about 1 wt. %, of pectin;

wherein
the total amount of sugar alcohol(s) is equal to or less than the total amount of saccharide compound (b),
the total amount of saccharide compound (b) is greater than the total amount of pectin, and
the total amount of sugar alcohol(s), inulin, and sclerotium gum is from at least 2.5 wt. % to about 6 wt. %;

(d) at least one water-soluble solvent selected from glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol, and mixtures thereof;

(e) at least 75 wt. % of water;

(f) from about 0.01 to about 10 wt. %, about 0.01 to about 8 wt. %, or about 0.05 to about 6 wt. % of carrageenan; and (g) optionally, at least one surfactant, preferably, at least one nonionic surfactant, for example, a nonionic surfactant selected from glyceryl esters, ethylene glycol esters, propylene glycol esters, sucrose esters of fatty acids, and PEG-40 hydrogenated castor oil;

all weights being based on the total weight of the hair cosmetic composition; and wherein, preferably, the composition is in the form of a spray.

In an embodiment, the viscosity of the compositions of the present disclosure can range from about 200 cps to about 1000 cps, or from about 300 cps to about 800 cps, or from about 350 cps to about 700 cps, or from about 350 cps to about 600 cps, including ranges and sub-ranges therebetween. The viscosity can be measured by any commercial viscometer or rheometer.

In an embodiment, the viscosity of the compositions of the present disclosure is measured at 20° C. on a Brookfield viscometer using an RV spindle #7.

In various embodiments, the viscosity of the compositions of the present disclosure is at about 200 cps, 225 cps, 250 cps, 275 cps, 300 cps, 325 cps, 350, cps, 375 cps, 400 cps, 425 cps, 450 cps, 475 cps, 500 cps, 525 cps, 550 cps, 575 cps, 600 cps, 650 cps, 700 cps, 750 cps, 800 cps, 850 cps, 900 cps, 950, or 1000 cps, at 20° C. as measured on a Brookfield viscometer, using an RV spindle #7.

In an embodiment, the compositions of the present disclosure are in the form of a leave-on product such as a styling/shaping product, leave-on product for curly hair (such as combing creams or combing gels or combing lotions), anti-frizz hair product, or rinse-off or leave-on mask product.

In some embodiments, the compositions of the present disclosure are applied on curly hair with the curl type ranging from wavy to curly, or curly to coily.

In an embodiment, the compositions of the present disclosure are in the form of a rinse-off product such as a mask product.

In an embodiment, the compositions of the present disclosure are in the form of a leave-on product such as a styling/shaping product.

In an embodiment, the compositions of the present disclosure are in the form of a leave-on product such as a styling/shaping and/or conditioning product.

In an embodiment, the compositions of the present disclosure are in the form of a leave-on or a rinse-off styling conditioner.

In an embodiment, the compositions of the present disclosure are in the form of a spray composition.

In an embodiment, the compositions of the present disclosure are in the form of non-aerosol spray (not containing propellants).

In an embodiment, the composition of the present disclosure can be in aerosol format wherein the composition is combined with one or more propellants.

In an embodiment, the compositions of the present disclosure are in the form of a solution or lotion or cream or a gel or an emulsion such as an oil-in-water emulsion or a water-in-oil emulsion.

Methods, Kits, and Packaging

Another aspect of the invention pertains to methods of using the hair cosmetic compositions described herein. The methods generally comprise applying any of the hair cosmetic compositions described to hair. The hair cosmetic compositions may be useful in a variety of settings, and either for chemically treated or untreated hair. Use on treated hair can include chemically relaxed/straightened hair or chemically dyed or bleached or lightened/highlighted hair. Use on hair may include as part of a shampoo, part of a conditioner or as a conditioner, as a pre-treatment, or after cleansing or conditioning or washing the hair as a leave-on treatment for styling/shaping the hair or caring for curly hair or as a leave-on or rinse-off mask treatment.

Methods of treating hair according to the disclosure may include applying a hair cosmetic composition of the instant disclosure to the hair (wet, damp, or dry hair), allowing the hair treatment to remain on the hair for a sufficient amount of time, and rinsing the hair cosmetic composition from the hair or allowing the hair treatment to be left on the hair as a leave-on product. The hair cosmetic composition may be applied to the hair before, during, or after other hair cosmetic compositions (e.g., a shampoo, a conditioner, a mask, a cream, a lotion, a gel, etc.).

Other methods of treating hair according to the disclosure involve a wash and go/braiding technique. Typically, the hair type on which this method is used is curly hair.

Other methods of treating hair according to the disclosure involve a twist out technique. Typically, the hair type on which this method is used is curly hair.

The hair cosmetic composition may be allowed to remain on the hair for a period of time, for example from about a few seconds (1, 3, 5, or 10 seconds) to about 10, 20, or 30 minutes, or from about one to about eight hours, or up to about 12 hours, or up to about 24 hours or up to about 48 hours, or overnight.

Described above is the individual application of a hair cosmetic composition or the combined or layered application of a hair cosmetic composition with another composition. In some cases, a hair cosmetic composition is individually applied to the hair and also combined or layered with another composition that is also applied to the hair.

The hair cosmetic compositions of the instant disclosure may be incorporated into a kit. For example, the kits may include at least one hair cosmetic composition according to the instant disclosure. The kits may also include one or more hair cosmetic compositions (according the instant disclosure), a shampoo and/or a conditioner and/or a mask.

The hair cosmetic compositions of the instant disclosure may be contained in a pump container or bottle or in a spray container or bottle. The spray bottle may be equipped with a valve for delivering the composition.

In one embodiment, the hair cosmetic composition of the present disclosure is in an aerosol or aerosolized format such that the composition is included in a container that also contains a propellant.

In one embodiment, the hair cosmetic composition of the instant disclosure is in an aerosol format and is included in a container that employs a bag-on valve (BOV) barrier packaging technology wherein the composition is contained separately from a propellant such as compressed air or other inert gas or nitrogen or other propellant. Typically, a BOV packaging is employed in a container such as an aluminum can that has an opening for crimping the valve; the valve is welded or connected to a foil based packaging bag. Typically, the foil based packaging is comprised of a film laminate. Once the valve is crimped, compressed gas is filled into the area between the bag and can ("cup gassing").

Implementation of the present disclosure is provided by way of the following examples. The examples serve to illustrate the technology without being limiting in nature.

Example 1—Invention Hair Cosmetic Composition (Spray-Type Hair Styling/Shaping Composition)

|  | INCI US Name | FORMULA A wt. % | B wt. % | C wt. % | D wt. % |
|---|---|---|---|---|---|
| (a) Sugar alcohol | SORBITOL | 1.5 | 1.5 | 1.5 | 1.5 |
| (b) Sugar | GLUCOSE | 2.0 | 2.0 | 2.0 | 2.0 |
|  | SUCROSE | 0.08 | 0.08 | 0.08 | 0.08 |
| (c) Pectin | PECTIN | 0.3 | 0.3 | 0.3 | 0.3 |
| (d) Water-Soluble Solvent | GLYCERIN AND/OR CAPRYLYL GLYCOL | 3.5-4.0 | 3.5-4.0 | 3.5-4.0 | 3.5-4.0 |
| Stabilizer/Thickening Agent | CARRAGEENAN | 0.1 | 0.1 | 0.1 | 0.1 |
| Vegetable Oil/Fruit Extract | VEGETABLE OIL AND/OR FRUIT EXTRACTS | ≤0.5 | ≤0.5 | ≤0.5 | ≤0.5 |
| Miscellaneous | NONIONIC SURFACTANT(S), PRESERVATIVE(S), VITAMIN(S), PERFUME(S), PH ADJUSTERS, FRAGRANCE SOLUBILIZERS, ETC. | ≤5 | ≤5 | ≤5 | ≤5 |
| (e) Water | WATER | Q.S. 100% | Q.S. 100% | Q.S. 100% | Q.S. 100% |

The viscosity of the formula A in Example 1 is about 400 cps at 20° C., as measured on a Brookfield viscometer using an RV Spindle #7.

Example 2 Comparative Composition (Hair Styling/Shaping Composition)

|  | INCI US Name | FORMULA | | |
|---|---|---|---|---|
|  |  | E (Gel) wt. % | F (Spray) wt. % | G (Spray) wt. % |
| Sugar alcohol | SORBITOL | 2.0 | 1.5 | 1.5 |
| Sugar | INULIN | 1.5 | — | 1.1 |
|  | GLUCOSE | — | 2.0 | — |
| Gum | SCLEROTIUM GUM | 0.5 | 0.3 | 0.3 |
| (d) Water-Soluble Solvent | GLYCERIN AND/OR CAPRYLYL GLYCOL | 5.0 | 4.0 | 4.0 |
| Stabilizer/Thickening Agent | CARRAGEENAN | 0.1 | 0.1 | 0.1 |
| Vegetable Oil/Fruit Extract | VARIES | ≤0.5 | ≤0.5 | ≤ 05 |
| Miscellaneous | NONIONIC SURFACTANT(S), PRESERVATIVE(S), VITAMIN(S), PERFUME(S), ETC. | ≤3 | ≤3 | ≤3 |
| (e) Water | WATER | Q.S. 100% | Q.S. 100% | Q.S. 100% |

The viscosity of formula F in Example 2 is about 1900 cps at 20° C. as measured on a Brookfield viscometer using an RV Spindle #6. The spindle size is different from that used for the formulas in Example 1 because the viscosity of the formulas in Example 2 are much higher.

Example 3

(Contribution of Main Components)

The individual influence of each of three main components of the hair styling composition of Example 1 (sugar alcohol (sorbitol), glucose, and pectin) was investigated.

The inclusion of sugar alcohol(s) in the hair styling compositions resulted in a product that imparts appreciable discipline to the hair. The sugar alcohol(s) increased the ease of distribution of the hair styling composition, providing uniform spreadability on the hair fibers.

Glucose provided hold and control to the hair. This natural-based ingredient provided similar hold/control properties as traditional synthetic hair styling polymers. Other sugar derivatives were explored such as inulin and maltodextrin. However, the use of these ingredients resulted in the curls being weighed down.

Pectin provided hydration and moisture with a soft touch feel. Other thickening agents such as sclerotium gum were explored. However, the use of sclerotium gum resulted in a gel texture that provided the hair with heavier coating. The use of pectin also allowed the composition to achieve a stable viscosity and spray fluidity which helped with batch scale ups.

The sugar alcohol(s) in combination with glucose and pectin resulted in the hair styling compositions that imparted defined curls, curl regularity, frizz control, shape/style control, shine, and soft touch.

It was also found that the formula can be applied on wet or damp curly hair to be air-dried and can also be used on the second (next) day as a refresher to reactivate the curls, providing definition, bounce, frizz control, and shine to the hair (durable styling or shaping benefits). All test formulas were used as leave-on formulas on hair.

Example 4

The formula is also designed in pump spray and Bag-On-Valve (BOV) aerosol spray formats which makes it easy and faster for curly consumers to apply the product on hair on a daily basis as a leave-on hair styling composition, especially as a product for refreshing the style and condition of hair several hours or the day after first application. For example, formulas A to D above were included in containers equipped with the BOV technology in which the BOV packaging bag was filled with compressed nitrogen. By applying the formulas on hair using the BOV aerosol type format, this format allowed the user to spray the formula in any direction in a 360 pattern and to apply the formula in a non-upright position thus making the application easier and more homogeneous on hair. Also, in a BOV aerosol format, the formula could be delivered by use of a propellant that was more environment-friendly (i.e., compressed nitrogen in contrast to other propellants such as butane, isobutane, or isopropane).

Example 5

(Cosmetic Attributes)

A consumer study of 58 volunteer subjects was conducted in which the volunteer subjects assessed the cosmetic benefits/attributes imparted by the invention composition to their hair based on a 9-point scale (1 being the most negative response and 9 being the most positive response). Formula D was used in the study as a leave-on composition. The assessments were done at different time points: Day 1—Immediately upon product application (wet hair); Day 1—End of Day 1 (dry hair); and Day 2—Immediately upon waking up (dry hair).

Results

| Day 1 - Immediately upon product application (wet hair) | Median (n = 58) | % Scale 6-9 |
|---|---|---|
| Product helps pre-style curls on wet hair | 7.0 | 79.3% |
| Product helps define curls | 7.0 | 75.9% |
| Hair does NOT feel weighed down | 8.0 | 91.4% |
| Hair feels soft | 8.0 | 87.9% |
| Hair feels moisturized | 8.0 | 82.8% |
| Overall Satisfaction | 8.0 | 81.0% |

| Day 1 - End of Day | Median (n = 58) | % Scale 6-9 |
|---|---|---|
| Product helps define curls | 7.0 | 84.5% |
| Hair does NOT feel weighed down | 7.5 | 89.7% |
| Product does NOT leave build up | 8.0 | 87.9% |
| Hair feels soft | 8.0 | 91.4% |
| Hair feels moisturized | 8.0 | 82.8% |
| Overall Satisfaction | 8.0 | 87.9% |

| Day 2 - Immediately upon waking up (dry hair) | Median (n = 58) | % Scale 6-9 |
|---|---|---|
| Product helps refresh curls on dry hair | 7.5 | 86.2% |
| Product helps define curls | 7.0 | 81.0% |
| Hair does NOT feel weighed down | 8.0 | 91.4% |
| Product does NOT leave build up | 8.0 | 84.5% |
| Hair feels soft | 8.0 | 93.1% |
| Hair feels moisturized | 8.0 | 86.2% |
| Overall Satisfaction | 8.0 | 89.7% |

It is evident from the very high ratings presented above, that the volunteer subjects found that the invention composition imparted very good cosmetic attributes to hair, namely, the composition helped define curls, did not weigh the hair down, did not build up a residue on hair, made the hair feel soft and moisturized at all the time points (Day 1—Immediately upon application (wet hair); Day 1—End of Day 1 & Day 2—Immediately upon waking up (dry hair). In addition, the composition helped with pre-styling the hair on Day 1 (immediately upon application—on wet hair) and it also helped refresh the curls on dry hair on Day 2, after the volunteer subjects have slept on their hair. On all time points, the volunteer subjects gave a high rating of 8.0 to the attribute of "overall satisfaction".

Example 6

(Cosmetic Attributes Against a Bench)

The hair styling composition A of Example 1 was evaluated by comparing its performance against a commercial benchmark product containing water, mineral oil, glycerin, cetearyl alcohol, cyclopentasiloxane, fragrance, phenoxyethanol, stearamidopropyl dimethylamine, 1, 2, hexanediol, polyquaternium crosspolymer-3, lactic acid, disodium EDTA, dimethiconol, dimethicone crosspolymer, tocopheryl acetate, silk amino acids. Six volunteers participated; they had medium-long hair, curl patterns or type ranging from wavy hair to medium-tight curls, hair has been subjected to chemical treatments (dye, relaxer, etc.). The volunteers' hair was shampooed. After shampooing, while the hair remained damp, the hair styling composition A of Example 1 was applied to half the head of each volunteer and the commercial benchmark product was applied to the other half of the head of each volunteer. After the hair was air dried, experts evaluated the hair. The experts ranked a variety of attributes on a numerical scale, in most cases a scale of 1 to 5, where high numbers (e.g., 5) indicate better results.

The inventive Composition A performed statistically significantly better than the Commercial Benchmark with respect to distribution on hair, speed of hair transformation, curl definition, curl regularity, frizz control, and smooth hair feel. The inventive Composition A was also observed to impart more discipline to hair and hydration to hair the day after an application.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

All percentages, parts and ratios herein are based upon the total weight of the compositions of the present disclosure, unless otherwise indicated.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 2% by weight of a specific material added to a composition, based on the total weight of the compositions. The components described for optional inclusion in the compositions of the disclosure may be free of the component(s) or may be "substantially free" or "essentially free" of the component(s). Nonetheless, the compositions may include less than about 1 wt. %, less than about 0.5 wt. %, less than about 0.1 wt. %, or none of the specified material.

The term "treat" (and its grammatical variations) as used herein refers to the application of the cosmetic compositions of the present disclosure onto the surface of the body, and in particular the skin and/or hair of the body.

The term "volatile", as used herein, means having a flash point of less than about 100° C.

The term "non-volatile", as used herein, means having a flash point of greater than about 100° C.

The term "substituted," as used herein, means comprising one or more substituents. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The term "polymers," as defined herein, include homopolymers and includes copolymers formed from at least two different types of monomers.

The methods and compositions of the present disclosure can comprise, consist of, or consist essentially of the essential elements and limitations of the disclosure described herein, as well as any additional or optional ingredients, components, or limitations described herein or otherwise useful. Additionally, any component that is positively set forth in the present disclosure can be negatively excluded from the methods and compositions of the present disclosure, and in particular from the claims of the present disclosure. In particular, the methods and compositions of the present disclosure can be free or essentially free of any component that is positively set forth in the present disclosure.

Other than in the operating examples, or where otherwise indicated, all numbers expressing quantities of ingredients and/or reaction conditions can be modified, if desired, with the term "about," meaning within +/−5% of the indicated number.

As used herein, all ranges provided are meant to include every specific range.

The terms "a," "an," and "the" are understood to encompass the plural as well as the singular. Thus, the term "a mixture thereof" is synonymous with "mixtures thereof." Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may include, or a mixture of any two of A, B, C, D, E, F, a salt of A, a salt of B, a salt of C, a salt of D, a salt of E, and a salt of F may be included.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular method or composition includes both a nonionic surfactant and a fatty compound, a single fatty acid will serve as only the nonionic surfactant or as only the fatty compound (the single fatty acid does not serve as both the nonionic surfactant and the fatty compound).

All publications, patents, and patent applications cited in the present disclosure are herein incorporated by reference, and for any and all purposes, as if each individual publication, patent, or patent application were specifically and individually indicated to be incorporated by reference. In the event of an inconsistency between the present disclosure and any publications, patents, or patent applications incorporated herein by reference, the present disclosure controls.

The invention claimed is:

1. A hair cosmetic composition comprising:
   (a) sorbitol;
   (b) an amount of at least one saccharide compound selected from sucrose, glucose, and a mixture thereof;
   (c) an amount of about 0.1 to about 3 wt. % of pectin; wherein
      the amount of (a) is equal to or less than the amount of (b);
      the amount of (b) is greater than the amount of (c); and
      a combined amount of (a), (b), and (c) is from at least 2 wt. % to about 8 wt. %;
   (d) an amount of at least one water-soluble solvent;
   (e) an amount of at least 80 wt. % of water;
   (f) an amount of at least one stabilizer and/or thickening agent; and
      wherein the hair cosmetic composition has a viscosity of about 200 to about 1000 cps at 20° C., and all weight percentages are based on a total weight of the hair cosmetic composition.

2. The hair cosmetic composition of claim 1, wherein the amount of the at least one saccharide compound of (b) is from about 0.1 to about 6 wt. %, based on the total weight of the hair cosmetic composition.

3. The hair cosmetic composition of claim 1, wherein the at least one water soluble solvent of (d) is an organic solvent selected from a short chain monoalcohol, a glycol, a polyhydric alcohol, and a mixture thereof.

4. The hair cosmetic composition of claim 1, wherein the total amount of the at least one water-soluble solvent of (d) is about 0.5 to about 15 wt. %, based on the total weight of the hair cosmetic composition.

5. The hair cosmetic composition of claim 1, wherein the at least one stabilizer and/or thickening agent of (f) is selected from acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sodium carboxymethyl dextran, sodium carrageenan, tragacanth gum, xanthan gum, biosaccharide gum, and mixtures thereof.

6. The hair cosmetic composition of claim 1, wherein the at least one stabilizer and/or thickening agent of (f) is carrageenan.

7. The hair cosmetic composition of claim 1, wherein the total amount of the at least one stabilizer and/or thickening agent of (f) is from about 0.01 to about 10 wt. %, based on the total weight of the hair cosmetic composition.

8. The hair cosmetic composition of claim 1, further comprising at least one nonionic surfactant.

9. The hair cosmetic composition of claim 6 comprising less than 0.1 wt. % of monohydric alcohols.

10. The hair cosmetic composition of claim 9 comprising less than 0.1 wt. % of synthetic film-forming polymers.

11. The hair cosmetic composition of claim 10 comprising less than 0.1 wt. % of silicones.

12. The hair cosmetic composition of claim 1 in a form of a spray.

13. A kit comprising the hair cosmetic composition of claim 1 in a spray container.

14. The kit of claim 13, wherein the spray container is a bag-on-valve equipped container.

15. The hair cosmetic composition of claim 1 being free from betaines.

16. The hair cosmetic composition of claim 1 being free from xanthan gum and modified xanthan gum.

17. A hair cosmetic composition comprising:
(a) an amount of about 1 to about 5 wt. % of sorbitol;
(b) an amount of about 1 to about 5 wt. % of at least one saccharide compound selected from sucrose, glucose, and a mixture thereof;
(c) an amount of about 0.1 to about 3 wt. % of pectin; wherein
the amount of (a) is equal to or less than the amount of (b);
the amount of (b) is greater than the amount of (c); and
a combined amount of (a), (b), and (c) is from at least 2 to about 8 wt. %;
(d) an amount of at least one water-soluble solvent selected from glycerin, ethylene glycol, diethylene glycol, triethylene glycol, propylene glycol, dipropylene glycol, tripropylene glycol, butylene glycol, caprylyl glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol, and mixtures thereof;
(e) an amount of at least 75 wt. % of water; and
(f) an amount of about 0.05 to about 6 wt. % of carrageenan;
wherein the hair cosmetic composition comprises less than 0.1 wt. % of synthetic film-forming polymers and less than 0.1 wt. % of silicones, and
all weight percentages are based on a total weight of the hair cosmetic composition.

18. The hair cosmetic composition of claim 17, wherein the hair cosmetic composition has a viscosity of from about 200 to about 1000 cps at 20° C.

19. The hair cosmetic composition of claim 17 being free from betaines.

20. The hair cosmetic composition of claim 17 being free from xanthan gum and modified xanthan gum.

21. The hair cosmetic composition of claim 17, further comprising at least one nonionic surfactant.

22. The hair cosmetic composition of claim 21, wherein the at least one nonionic surfactant is polyoxyalkylenated or polyglycerolated.

23. A hair cosmetic composition consisting of:
(a) an amount of about 1.2 to about 4 wt. % of sorbitol;
(b) an amount of about 1.2 to about 4 wt. % of sucrose, glucose, or a mixture thereof;
(c) an amount of about 0.1 to about 1.8 wt. % of pectin; wherein
the amount of (a) is equal to or less than the amount of (b);
the amount of (b) is greater than the amount of (c); and
a combined amount of (a), (b), and (c) is from at least 2.5 to about 8 wt. %;
(d) an amount of at least one water-soluble solvent selected from glycerin, ethylene glycol, diethylene glycol, triethylene glycol, propylene glycol, dipropylene glycol, tripropylene glycol, butylene glycol, caprylyl glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol, and mixtures thereof;
(e) an amount of at least 75 wt. % of water;
(f) an amount of about 0.05 to about 6 wt. % of carrageenan;
(g) optionally, an amount of 5 wt. % or less of one or more vegetable oils, fruit extracts, or a mixture thereof;
(h) optionally, an amount of 5 wt. % or less of one or more miscellaneous ingredients chosen from nonionic surfactants, preservatives, vitamins, perfumes, pH adjusters, fragrances, and a mixture thereof;
wherein all weight percentages are based on a total weight of the hair cosmetic composition.

24. A method for styling hair comprising applying the hair cosmetic composition of claim 1 to the hair.

25. The method of claim 24, wherein the hair cosmetic composition is applied to the hair by spraying the hair cosmetic composition onto the hair.

* * * * *